United States Patent
Häuselmann et al.

(10) Patent No.: US 7,772,000 B2
(45) Date of Patent: Aug. 10, 2010

(54) METHOD AND APPARATUS FOR MECHANICAL STIMULATION OF TISSUE IN VITRO

(75) Inventors: Hans Jörg Häuselmann, Bellariastrasse 38, Zürich (CH) CH-8038; Markus Muser, Wädenswil (CH); Peter Niederer, Zürich (CH); Martin Stoddart, Zürich (CH); Erik Hedbom, Zürich (CH)

(73) Assignee: Hans Jörg Häuselmann, Zurich (CH)

(*) Notice: Subject to any disclaimer, the term of this patent is extended or adjusted under 35 U.S.C. 154(b) by 1256 days.

(21) Appl. No.: 11/284,146

(22) Filed: Nov. 21, 2005

(65) Prior Publication Data

US 2006/0129071 A1    Jun. 15, 2006

Related U.S. Application Data (63) Continuation of application No. PCT/IB03/02153, filed on May 23, 2003.

(51) Int. Cl.
*C12N 5/00* (2006.01)
*C12M 1/00* (2006.01)

(52) U.S. Cl. .................................. 435/375; 435/283.1
(58) Field of Classification Search ........................ None
See application file for complete search history.

(56) References Cited

U.S. PATENT DOCUMENTS 5,153,136 A    10/1992    Vandenburgh
5,217,899 A    6/1993    Shapiro et al.
5,348,879 A    9/1994    Shapiro et al.
5,882,929 A    3/1999    Fofonoff et al.
6,066,495 A    5/2000    Fofonoff et al.
6,107,081 A    8/2000    Feeback et al.
7,553,662 B2 *  6/2009    El Haj et al. ................. 435/373

OTHER PUBLICATIONS

Stoddart et al., "Enhanced Matrix Synthesis in De Novo, Scaffold Free Cartilage-Like Tissue Subjected to Compression and Shear", Biotechnology and Bioengineering 95 (6) :1043-1051 (2006).*
Waldman et al., "Multi-axial mechanical stimulation of tissue engineered cartilage: review", European Cells and Materials 13 : 66-75 (2007).*
International Search Report from corresponding PCT/IB03/02153 dated Apr. 5, 2004.

* cited by examiner

*Primary Examiner*—Sandra E Saucier
(74) *Attorney, Agent, or Firm*—Marshall, Gerstein & Borun LLP (57) ABSTRACT

The invention concerns a method and an apparatus for mechanical stimulation in vitro of tissue, wherein tissue patches (1) are retained in a tissue carrier (2), thereby presenting first surfaces (3) to be stimulated in a plane (X) and wherein a roller (4) having a second surface (5) arranged at its periphery is moved parallel to said plane (X), thereby imposing selected forces on said first surfaces (3) by said second surface (5) for stimulating the tissue patches (1). By presenting the surfaces (3) to be stimulated in a common plane (X) and by moving the roller (4) parallel to said common plane (X) of the first surfaces (3), serving several tissue carriers (2) with one roller (4) is made easy, thus integration into an industrial production is made practicable.

18 Claims, 11 Drawing Sheets

METHOD AND APPARATUS FOR MECHANICAL STIMULATION OF TISSUE IN VITRO

RELATED APPLICATION DATA

This is a continuation of International Patent Application No. PCT/IB2003/002153 filed 23 May 2003.

TECHNICAL FIELD

The invention concerns a method and an apparatus for mechanical stimulation of tissue in vitro as well as a tissue carrier for retaining tissue patches during mechanical stimulation in vitro according to the preambles of the independent claims.

BACKGROUND ART

It is well known that musculoskeletal tissues cultivated in vitro, due to their unique ability to respond to mechanical load, can be optimized and "trained" for their later in vivo use, e.g., as implant, by subjecting them, during their cultivation, to specific mechanical load patterns.

In U.S. Pat. No. 5,882,929 there are disclosed several apparatuses and methods for subjecting a biopolymer tissue construct in vitro to selected forces, like e.g., to shear forces, frictional forces, torsional forces or compressive forces or combinations thereof, respectively. In order to do so, the tissue is mounted on a tissue carrier and is then mechanically stimulated by plunger type or roller type stimulating means. With the apparatuses having plunger type stimulating means, small tissue patches can be stimulated, while with those having roller type stimulating means, large tissue surfaces arranged at the inside of cylindrical tissue carriers can be stimulated. However, efficiently integrating the latter into an automated industrial production is almost impossible, since it is difficult to serve multiple of cylindrical tissue carriers with one stimulating apparatus and to safely mount tissue at these tissue carriers, in particular in case a plurality of individual tissue patches is concerned.

DISCLOSURE OF THE INVENTION

Hence, it is a general object of the invention to provide a method, an apparatus and a tissue carrier which do not have the before mentioned disadvantages.

A first aspect of the invention concerns a method for mechanical in vitro stimulation of tissue. According to one step of the method, one or several tissue patches are provided which are retained in a tissue carrier in such a manner that each of them presents a first surface to be stimulated. According to another step of the method, roller type stimulating means are provided which have arranged at their outer periphery one or several second surfaces. According to yet another step of the method, said roller type stimulation means and said tissue carrier are moved relative to each other in such a manner that specific forces, like e.g. shear forces, frictional forces with or without sliding, torsional forces, squeezing forces, compressive forces or combinations thereof, are imposed on said first surfaces of said tissue patches through said second surfaces of said roller type stimulating means for mechanically stimulating said tissue patches.

By retaining the tissue patches in the tissue carrier in such a manner that their first surfaces are presented in a common plane and by moving the roller type stimulating means during stimulation of the tissue patches parallel to said common plane, safely mounting tissue patches on tissue carriers and serving several tissue carriers with one stimulating tool is made easy, thus an integration of this stimulating method into an automated industrial production is made practicable.

In a preferred embodiment of the method, the relative movement between the roller type stimulating means and the tissue carrier includes a rotation of said roller type stimulating means around its axis, wherein said roller type stimulating means is preferably rotated at such a rotational speed that its circumferential speed, i.e. the circumferential speed at its second surfaces, at least temporarily differs from the speed of relative movement parallel to the common plane of the first surfaces. By doing so, the movement of the roller type stimulating means relative to said tissue carrier is not an ideal rolling motion but generates shear forces between said first and second surfaces.

This is, in one preferred embodiment, achieved by mechanically coupling the rotation of the roller type stimulating means to the relative movement between the tissue carrier and the roller type stimulating means parallel to the common plane of the first surfaces, resulting in a mechanical compulsory link between both movements. Linking these movements in this fashion has the advantage that no separate controls are necessary.

In another preferred embodiment, this is achieved by using drive means for rotating the roller type stimulating means which are not mechanically coupled with means for effecting the rest of relative movement between the roller type stimulating means and the tissue carrier but can separately be controlled, leading to a high flexibility in adjusting the relative movement and, as a result thereof, to flexible stimulation patterns. Preferably, those separate drive means for rotating said roller type stimulating means comprise an electric motor with individual speed and/or torque control.

In yet another preferred embodiment, this is achieved by rolling said roller type stimulating means with its second surfaces in frictional contact over said first surfaces and/or over further surfaces, e.g. a receiving surface of the tissue carrier, during said relative movement between tissue carrier and roller type stimulating means parallel to the common plane of the first surfaces. In a case where shear forces shall be generated between the first surfaces of the tissue patches and the second surfaces of the roller type stimulating means, the rolling motion of the roller type stimulating means is obstructed by applying brake forces opposing the rotation of said roller type stimulating means around its axis, e.g. by using a frictional brake. In this fashion, controlled shear forces can be imposed on the tissue patches in a very cost effective manner.

Preferably, a tissue carrier is used in the method according to the first aspect of the invention which is made of an elastic or visco elastic material and has a receiving surface in which one or several recesses or cavities are formed for retaining the tissue patches therein in such a manner that their first surfaces and the receiving surface are arranged within a common plane, thus substantially forming one common surface. This results in the tissue patches being safely retained within the tissue carrier.

When imposing shear forces on the first surfaces of the tissue patches arranged in a common plane with the receiving surface, the elastic or visco elastic material of said tissue carrier can experience a deformation caused by shear forces imposed on its receiving surface. Since such a deformation might adversely affect the safe retainment of tissue patches in the tissue carrier, it is advantageous to temporarily release said shear forces, e.g. at certain intervals, in order to allow a relaxation of this deformation.

In one preferred embodiment, this release of shear forces is accomplished by temporarily spacing apart said roller type stimulating means from the receiving surface. If this is performed through a guided movement of the roller type stimulating means along an actuating cam, a safe operation results thanks to the mechanical compulsory linkage of the movements.

In another preferred embodiment, this release of shear forces is accomplished by temporarily releasing a rotational driving force or a brake force applied to said roller type stimulating means. This method offers the benefit of being highly flexible.

In yet another preferred embodiment of the method according to the first aspect of the invention, a deformable diaphragm is arranged between said first surfaces and said second surfaces, for allowing a mechanical stimulation of the tissue patches with the roller type stimulating means while forming an aseptic barrier between them. This is in particular of importance in case several tissue carriers are to be served by one roller type stimulating means, in which case it is furthermore preferred when the diaphragm is part of the tissue carrier.

Preferably, the method is used for mechanically stimulating tissue patches which have been produced in vitro, which are of a cartilage or cartilage derived tissue and/or which are part of tissue/bone composites, because in such use the advantages of this method clearly become evident.

Furthermore, it is preferred to individually control, preferably by computerized control means, at least said parallel relative movement and the rotation of said roller type stimulating means, advantageously all relative movements between the roller type stimulating means and the tissue carrier. If in addition the forces generated between the second surfaces and the first surfaces and/or the receiving surface are measured and adjusted to predetermined values by controlling the relative movement between roller type stimulating means and tissue carrier, a high flexibility can be achieved.

A second aspect of the invention concerns an apparatus for mechanical stimulation of tissue in vitro which preferably can be used for performing the method according to the first aspect of the invention. The apparatus comprises a tissue carrier, a roller type stimulating means and actuating means. The tissue carrier is adapted for enabling retainment of one or several tissue patches in such a manner that they present one or several first surfaces in a common plane. The roller type stimulating means has arranged at its periphery one or several second surfaces for acting on said first surfaces. The actuating means are adapted for effecting a relative movement, which includes a relative movement parallel to said common plane of the first surfaces, between the tissue carrier and the roller type stimulating means, thereby generating specific forces or mechanical loading pattern, respectively, between the first and second surfaces for mechanical stimulation of the tissue patches. With such an apparatus, mechanical stimulation of tissue in vitro can be automated and performed on an industrial scale.

In a preferred embodiment of the apparatus, the actuating means are adapted to effect a rotation of said roller type stimulation means around its axis. Preferably, the actuating means are in position to rotate said roller type stimulation means during relative movement parallel to said plane at a circumferential speed that differs from the speed of relative movement between the roller type stimulating means and the tissue carrier parallel to the common plane of the first surfaces. Thus, a relative movement which differs from an ideal rolling motion is achieved between the roller type stimulating means and the tissue carrier, which generates shear forces between the first and second surfaces.

For effecting the rotation of the roller type stimulating means, the actuating means can comprise mechanical coupling means for establishing a compulsory mechanical link between the rotation of the roller type stimulating means and the relative movement between the roller type stimulating means and the tissue carrier parallel to the common plane of the first surfaces. The mechanical coupling means preferably include a driving wheel which is connected to and preferably mounted on the roller type stimulation means for driving the same. The driving wheel is, dependent on its embodiment, frictionally or positively coupled to a frictional pathway, a gear rod or a section of a chain, which is, at least during the relative movement parallel to said common plane of the first surfaces, stationary with respect to the tissue carrier. This embodiment has the advantage that a rotation of the roller type stimulating means is automatically effected once there is a relative movement between the roller type stimulating means and the tissue carrier parallel to the common plane of the first surfaces, thereby ensuring a reliable operation.

If the actuating means of the apparatus comprise separately controllable drive means for rotating the roller type stimulating means, e.g. an electrical motor with electronic controls for speed and/or torque, a high degree of flexibility to adapt the relative movement to specific requirements is achieved.

It is furthermore preferred when the actuating means are adapted to effect, during the relative movement between the roller type stimulating means and the tissue carrier parallel to the common plane of the first surfaces, a rotation of said roller type stimulation means around its axis through rolling it with its second surfaces in frictional contact over said first surfaces and/or further surfaces, like e.g. a receiving surface of the tissue carrier. In this case, it is of advantage when the actuating means furthermore comprise torque means, e.g. an electrical drive or a frictional brake, for generating a torque opposing the rotation of the roller type stimulating means and thereby generating, in a cost effective manner, specific shear forces between said first and second surfaces.

In another preferred embodiment of the apparatus, its tissue carrier has a planar receiving surface with one or several recesses in it for receiving and mounting the tissue patches therein. The receiving surface is formed by an elastic or visco elastic material and is substantially parallel to or arranged in the common plane of the first surfaces. Such a tissue carrier enables a safe mounting of the tissue patches during mechanical stimulation.

When the apparatus is equipped with the before mentioned tissue carrier and the actuating means are adapted to generate shear forces between the second surfaces of the roller type stimulating means and the receiving surface of the tissue carrier, it is preferred that the actuating means are furthermore adapted to allow, during the or following a relative movement between the roller type stimulating means and the tissue carrier parallel to the common plane of the first surfaces of the tissue patches, a temporary release of said shear forces to relax a deformation of said elastic or visco elastic material of said tissue carrier caused by said shear forces, thereby re-establishing the initial mounting situation of the tissue patches.

To facilitate this, the actuating means can be adapted to temporarily space apart the roller type stimulating means from the receiving surface, the roller type stimulation means can be embodied as a cylinder or cone having arranged at its periphery at least one flattening, which during rotation of said roller type stimulation means temporarily forms a gap between the second surfaces and the receiving surface or the actuating means can be adapted to temporarily release a rotational driving or braking force applied to said roller type stimulation means.

In yet another preferred embodiment the apparatus comprises a deformable diaphragm which is arranged between the first surfaces and the second surfaces to form an aseptic barrier between the tissue patches and the roller type stimulating means.

Further preferable embodiments of the apparatus comprise control means, preferably programmable computer control means for controlling, in open or closed loop operation, the relative movement between said tissue carrier and said roller type stimulating means. It is furthermore advantageous when they additionally comprise sensor means connected with said control means for measuring the forces generated between said second surfaces and said first surfaces and/or said receiving surface, and in particular for controlling these forces through said control means. Such an apparatus can be easily and repeatedly be adapted to predetermined stimulating cycles.

A third aspect of the invention concerns a tissue carrier for safely retaining tissue patches during mechanical stimulation in vitro and preferably for use in the method according to the first aspect of the invention or for the apparatus according to the second aspect of the invention. The tissue carrier has a planar, concave or convex receiving surface formed by an elastic or visco elastic material and has arranged within said receiving surface one or several recesses for receiving and mounting said tissue patches at said tissue carrier. Such a tissue carrier allows for a safe mounting of tissue patches during mechanical stimulation.

In a preferred embodiment of the tissue carrier, the recesses form cavities which widen in a direction from the receiving surface to the bottom of the cavities, thereby enabling a fixation of tissue patches in said recesses through positive locking.

Preferably, these cavities have a conical shape, preferably with a circular or polygonal, in particular with a hexagonal cross section.

In another preferred embodiment of the tissue carrier, the walls of the recesses comprise circumferential grooves or toothing for facilitating a positive fixation of the tissue patches in the recesses.

In yet another preferred embodiment, the part of the tissue carrier providing the receiving surface and the recesses is formed by a slab of elastic or visco elastic material, in particular by a silicone slab, which preferably has been formed by casting. The recesses may end within the slab or might extend through it in a direction substantially perpendicular to the receiving surface. Such slabs can be manufactured in large numbers at low cost as consumable parts.

BRIEF DESCRIPTION OF DRAWINGS

The invention will be better understood and objects other than those set forth above will become apparent when consideration is given to the following detailed description thereof. Such description makes reference to the annexed drawings, wherein.

MODES FOR CARRYING OUT THE INVENTION

Figure 1:
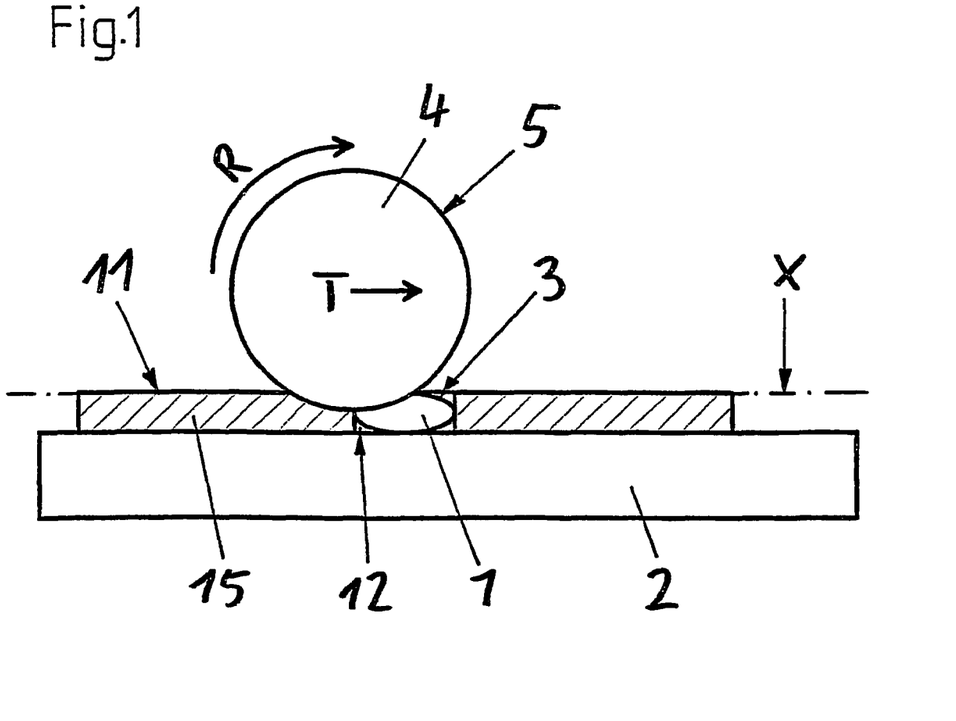
FIG. 1 shows a schematic diagram of a first stimulating method according to the invention.

The general concept of the invention can schematically be explained with the help of FIG. 1. A patch 1 of cartilage tissue is retained in a recess 12 in the receiving surface 11 of a tissue carrier 2 in such a manner that it presents a first surface 3 to be stimulated in a plane X. The receiving surface 11 is formed by a flat slab 15 of elastic or visco elastic material, e.g. of rubber, silicone, polyurethane or latex, and extends in the plane X. A roller type stimulating means 4 in the form of a cylindrical roller 4 is rolled with a second surface 5 arranged at its periphery over the receiving surface 11 and over the first surface 3, thereby effecting a rotation R of the roller 4 around its axis and a travelling motion T of it relative to the tissue carrier 2 parallel to said plane X. Since the roller 4 is, during rolling, pressed against the receiving surface 11 and the first surface 3 with a specific force, compressive and squeezing forces are imposed on these surfaces 3, 11 through the second surface 5, which stimulate the tissue patch 1.

Figure 2:
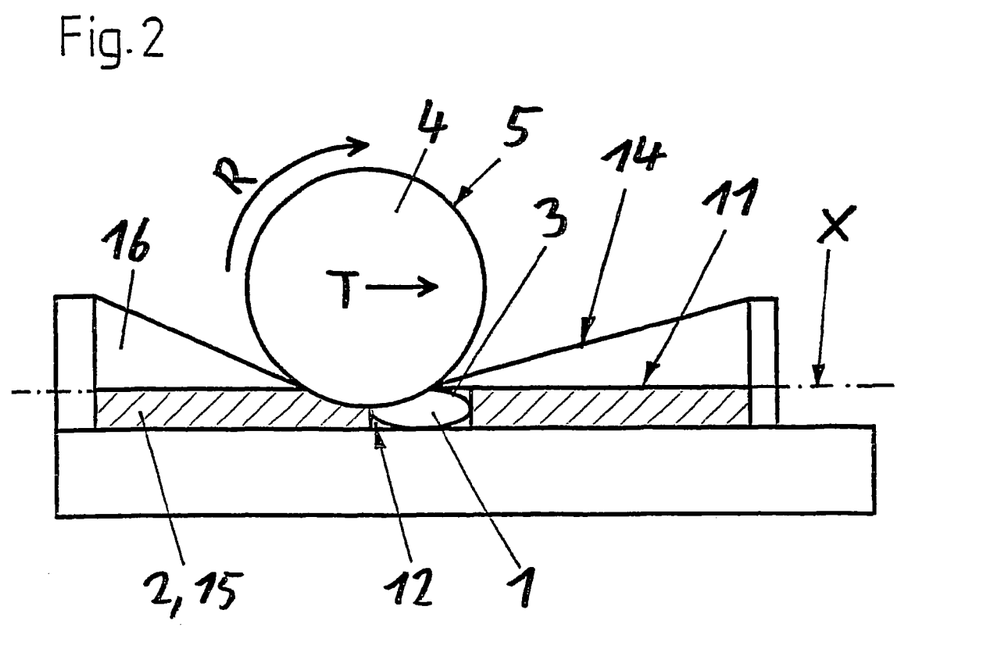
FIG. 2 shows a schematic diagram of a second stimulating method according to the invention.

The same principle is shown in FIG. 2, however with the difference that between the second surface 5 of the roller 4 and the receiving surface 11 of the tissue carrier 2 and the first surface 3 of the tissue patch 1 there is arranged a deformable diaphragm 14 of elastic material, e.g., of latex or rubber, which forms an aseptic barrier. By this measure, a sterile zone 16 is formed around the tissue patch 1 which considerably reduces the risk of infecting the tissue 1 during the stimulation cycle and enables a stimulation of tissue patches retained in different tissue carriers with the same roller 4 without the risk of crosswise contamination. The sterile zone might be filled with a specific gas and/or with a specific liquid, e.g., a nutrient solution, and might furthermore be fully conditioned with respect to e.g., temperature, humidity and pressure. It is of advantage when the tissue carrier 2 and the diaphragm 14 together form a closed sterile container module which can be automatically handled. In this case, it is easy to set up an industrial scale stimulating plant by automatically and in predetermined intervals feeding a number of such modules to a common stimulating machine.

Figure 3:
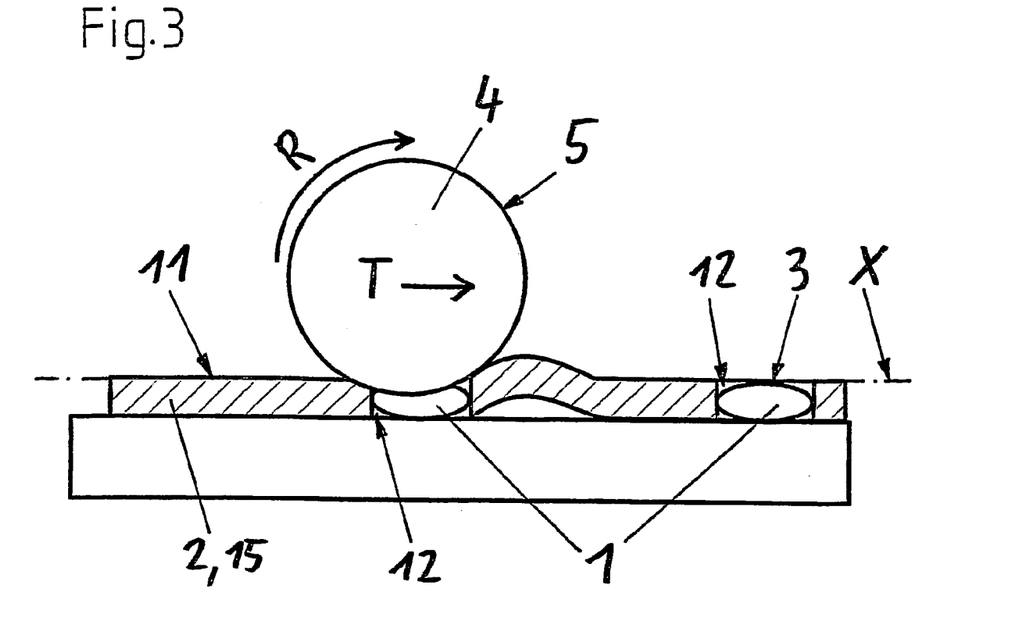
FIG. 3 shows a schematic diagram of a third stimulating method according to the invention.

FIG. 3 shows a stimulating principle similarly to the one of FIG. 1. In this diagram, two tissue patches 1 are retained in the tissue carrier 2, thereby each presenting a first surface 3 in a common plane X. In contrast to the principle shown in FIG. 1, a brake force is applied to the roller 4 which opposes its free rotation initiated by its frictional contact with the receiving surface 11 and/or the first surfaces 3 during its travelling motion T parallel to the plane X. Thus, its rotational speed is reduced with respect to a free rolling motion, which results in a difference between its circumferential speed and the speed of its travelling motion T parallel to the plane X and thereby causes shear forces between the second surface 5 and the receiving and first surfaces 11, 3. These shear forces in turn cause the slab 15 to bulge in front of the roller 4. In order to ensure a proper mounting of the tissue patches 1 in the tissue carrier 2, this shear forces or deformations, respectively, should frequently be released, e.g. by temporarily releasing the brake force or spacing apart the second surface 5 of the roller 4 from the receiving surface 11 of the tissue carrier 2.

Figure 4:
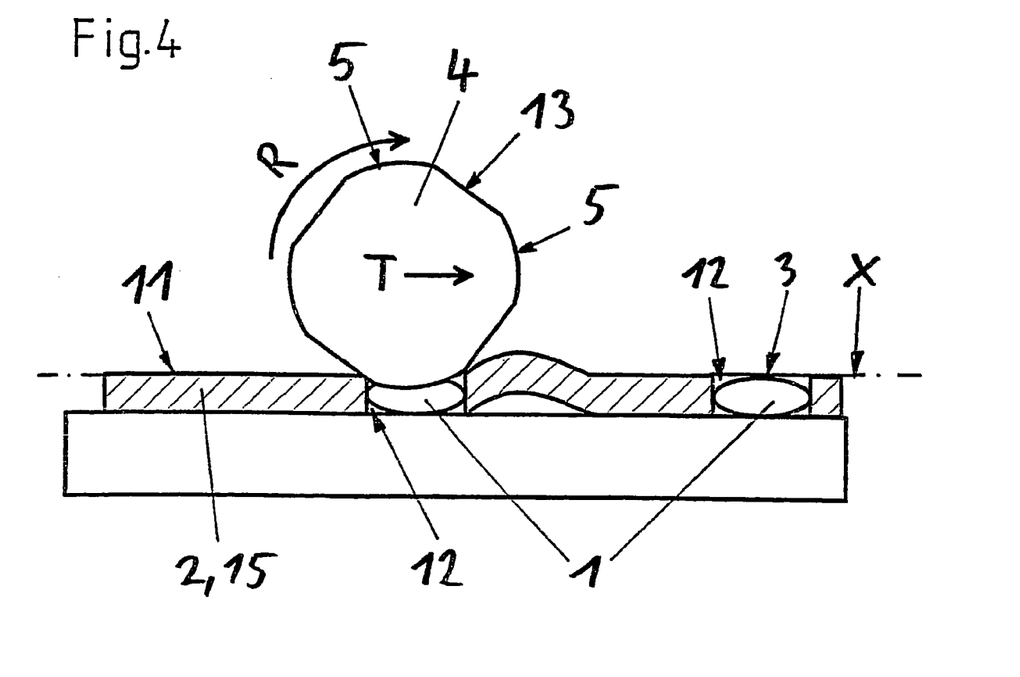
FIG. 4 shows a schematic diagram of a fourth stimulating method according to the invention.

FIG. 4 shows a stimulating principle wherein a roller 4 is used which has, equally distributed at its periphery, four flattenings 13, each of which separating two adjacent second surfaces 5. The roller 4 is moved parallel to the receiving surface 11 or the plane X, respectively, and at the same time is rotated by separate drive means (not shown) around its axis. The speed of rotation R is such that its circumferential speed at its second surfaces 5 is lower than the speed of its travel motion T parallel to the plane X, thereby causing shear forces between the second surfaces 5 and the receiving and first surfaces 11, 3 and subsequently a bulging deformation of the slab 15 in front of the roller 4. Once a first surface 3 of a tissue patch 1 has been stimulated by a second surface 5 of the roller 4, this second surface 5 is, due to the rotation R of the roller 4 during travel motion T, followed by a flattening 13 which generates a gap between roller 4 and receiving surface 11 and thereby allows a release of the shear forces and relaxation of the deformation of the slab 15. During further travel motion T and rotation R, the next second surface 5 of the roller 4 is brought in frictional contact with the next first surface 3 and the receiving surface 11 and again generates compressive forces, squeezing or kneading forces, respectively, and shear forces between the second surface 5 and these surfaces 3, 11.

Figure 5:
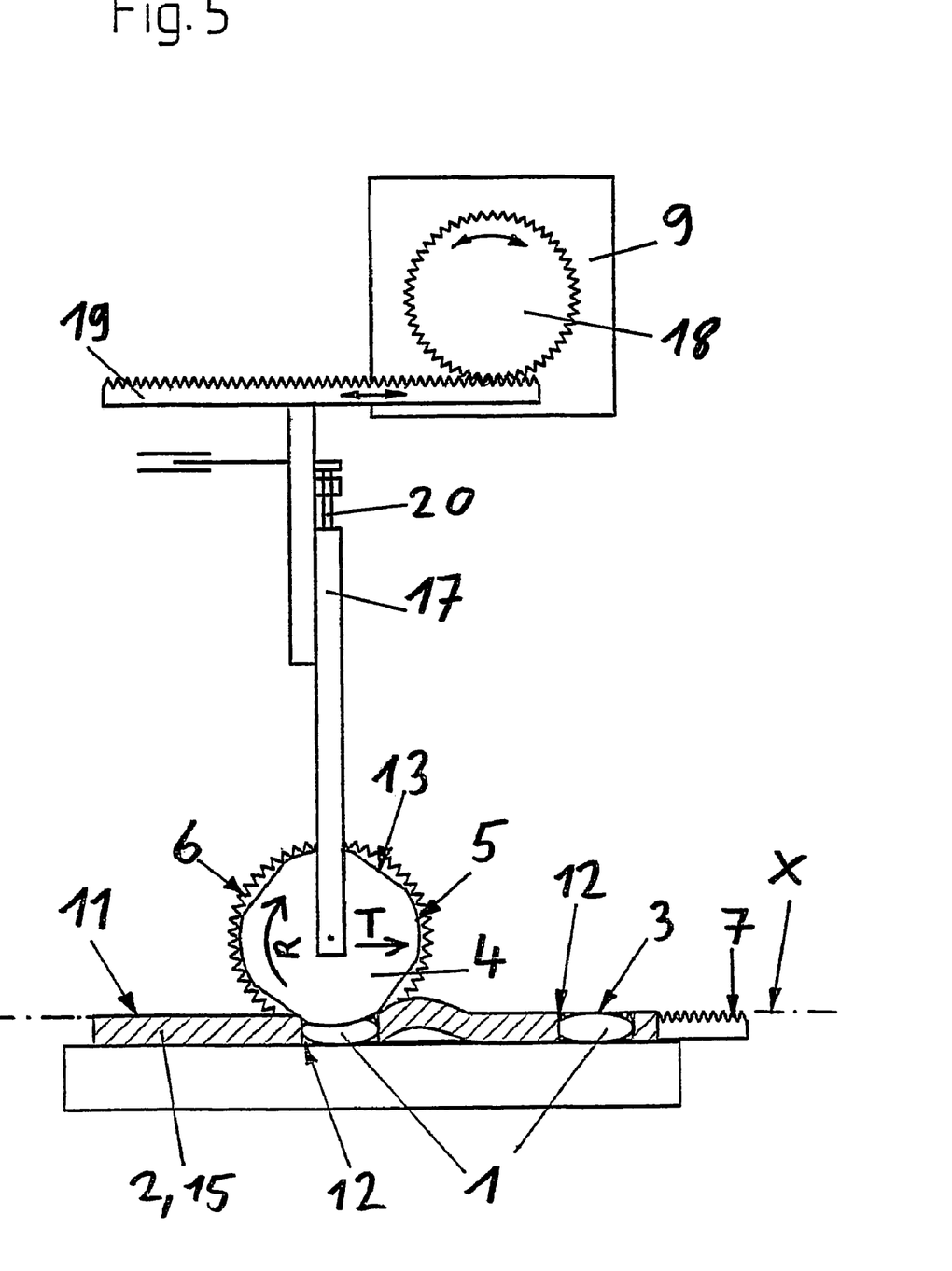
FIG. 5 shows a schematic diagram of a first stimulating apparatus according to the invention.

FIG. 5 shows a schematic diagram of a stimulating apparatus which operates according to the principle disclosed in FIG. 4. The apparatus comprises, beside the tissue carrier 2 and the roller 4 known from FIG. 4, a support structure 17 for supporting and enabling a guided movement of the roller 4 parallel and perpendicular to the plane X in which the receiving surface 11 of the tissue carrier 2 and the first surfaces 3 of the tissue patches 1 to be stimulated are located. The support structure can be moved parallel to the plane X by an electric motor 9 with encoder, which drives a gearwheel 18 that in turn moves a gear rod 19 which is mounted to the support structure 17, thereby also moving the roller 4 parallel to said plane X. The position of the roller 4 perpendicular to the plane X can manually or automatically be adjusted by means of an adjusting screw 20, thereby allowing an adjustment of the compressive forces between the second surfaces 5 of the roller 4 and the receiving surface 11 of the tissue carrier 2 and/or the first surfaces 3 of the tissue patches 1. In case of an automatic adjustment it is preferred to perform adjustment in closed loop control by measuring the compressive forces, e.g, by means of pressure sensors positioned under the tissue patches 1 in the tissue carrier 2. The roller 4 is at one end thereof equipped with a gear wheel 6 which has a bigger effective pitch circle diameter than the diameter of the roller 4 defined by its second surfaces 5 and which engages the teeth of a gear rod 7 that extends parallel to the plane X and is mounted on the tissue carrier 2. By this, the roller 4 is automatically rotated when it is moved parallel to the plane X by the motor 9 via the support structure 17. Due to the difference between the effective pitch circle diameter of the gear wheel 6 and the diameter of the roller 4 defined by its second surfaces 5, the circumferential speed of the roller 4 differs from its speed of travel parallel to the plane X or to the receiving surface 11 and the first surfaces 3, respectively, thereby generating not only compressive and squeezing forces but also shear forces between the surfaces 3, 5, 11 which continuously increase with the distance traveled parallel to the plane X until they are released by one of the flattenings 13 in the manner described earlier.

Figure 6:
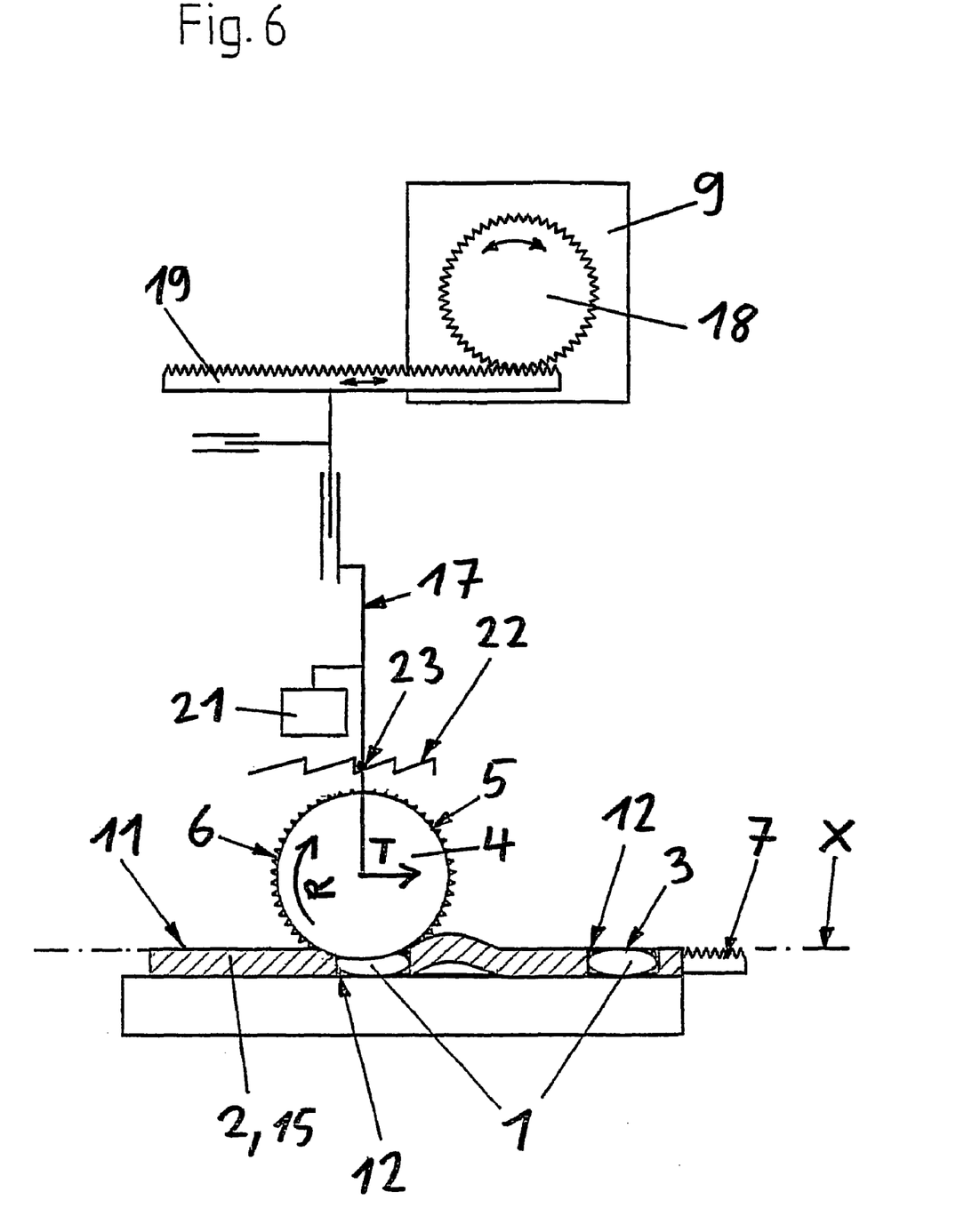
FIG. 6 shows a schematic diagram of a second stimulating apparatus according to the invention.

FIG. 6 shows a schematic diagram of a stimulating apparatus which is, with regard to the mechanism for generating the rotation R of the roller 4 and the translatory movement T of it parallel to the plane X, quite similar to the one of FIG. 5. The main difference exists in the way the compressive forces are generated and the shear forces are released. Instead of the adjusting screw 20, which adjusts the position of the roller 4 perpendicular to the plane X, in this embodiment a vertical guide with an interchangeable pressing weight 21 is used. The roller has no flattenings 13 but is embodied as a cylindrical roller 4 with one continuous second surface 5, as already known from the FIGS. 1 to 3. While travelling parallel to the plane X, a cam follower 23 mounted to the part of the support structure 17 which bears the roller 4 travels along a cam pathway 22. By doing so, it lifts, in intervals, this part of the support structure 17 together with the roller 4 against the gravitational force of the pressing weight 21 and thereby releases the shear forces through spacing apart the roller 4 from the tissue carrier 2. In contrast to the embodiment shown in FIG. 5, in which the relative small adjustment range in direction perpendicular to the plane X can be absorbed in the toothing of the gearwheel 6 and the gear rod 7, in this case it is recommended, however not absolutely necessary, to track the vertical movement of the gearwheel 6 with the guide rod 7, which is accomplished by pressing it against the gear wheel 6 by spring means.

It is obvious for someone skilled in the art that, instead of the gearwheels 6 with gear rods 7, e.g. chain wheels with chains or a friction wheels which travel on frictional pathways can be used and that the shear forces and the direction of it can be varied by varying the effective diameter of these wheels.

Figure 7:
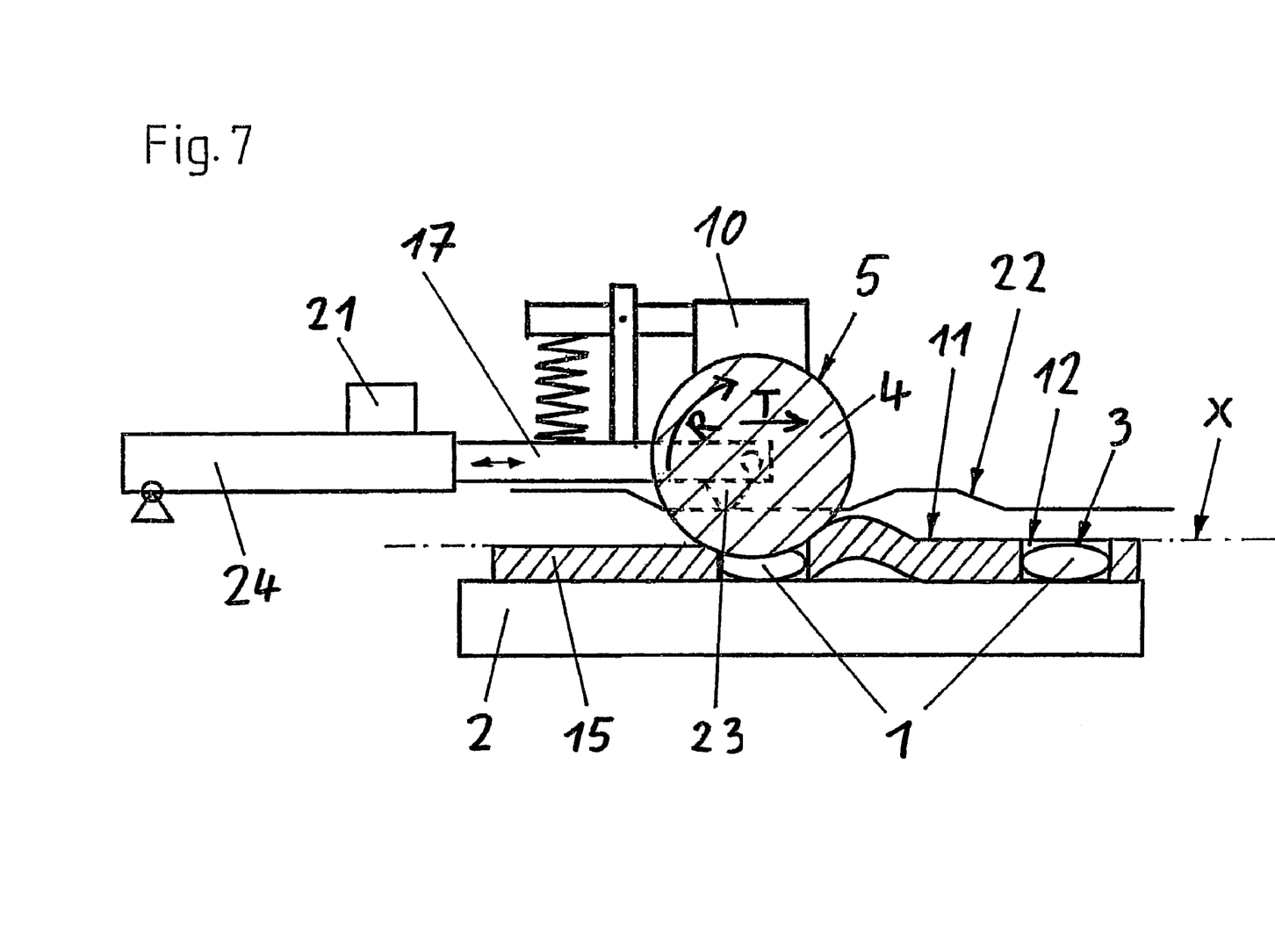
FIG. 7 shows a schematic diagram of a third stimulating apparatus according to the invention.

FIG. 7 shows a schematic diagram of a stimulating apparatus which operates according to the principle disclosed in FIG. 3. The apparatus comprises, beside the tissue carrier 2 and the roller 4 known from FIG. 3, a support structure 17 comprising a linear drive 24 for supporting and moving the roller 4 parallel to the plane X in which the receiving surface 11 of the tissue carrier 2 and the first surfaces 3 of the tissue patches 1 are located. The support structure 17 further comprises an interchangeable pressing weight 21 for adjusting the compressive forces imposed on the first surfaces 3 and the receiving surface 11 by the roller 4 and a torque means 10 in the form of a frictional brake 10, which generates a specific brake torque opposing the rotation R of the roller 4. While traveling parallel to the plane X, the roller with its second surface 5 not only imposes compressive and squeezing forces on these surfaces 3, 11, but, due to the brake torque generated by the frictional brake 10, also shear forces which are, in contrast to the before discussed embodiments constant and not increasing while travelling parallel to the plane X. As already known from the embodiment shown in FIG. 6, a cam follower 23 (indicated by dotted lines) mounted to the part of the support structure 17 which bears the roller 4 travels, during this parallel movement T, along a cam pathway 22 which is mounted on the tissue carrier 2, thereby lifting, at certain locations, the support structure 17 together with the roller 4 against the gravitational force of the pressing weight 21 and releasing the shear forces through spacing apart the roller 4 from the tissue carrier 2.

Figure 8:
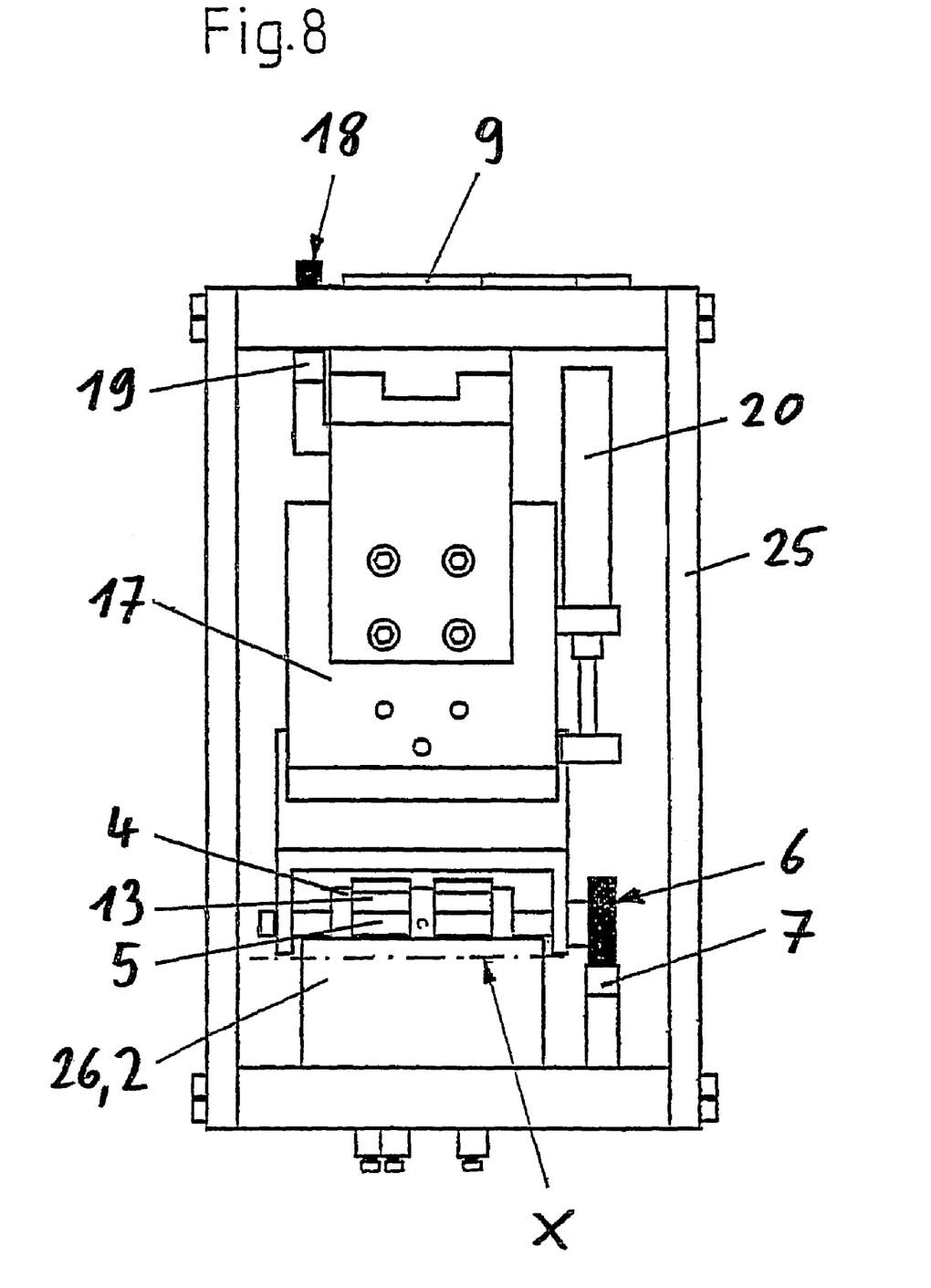
FIG. 8 shows a front view of a first embodiment of a stimulating apparatus according to the invention.
Figure 9:
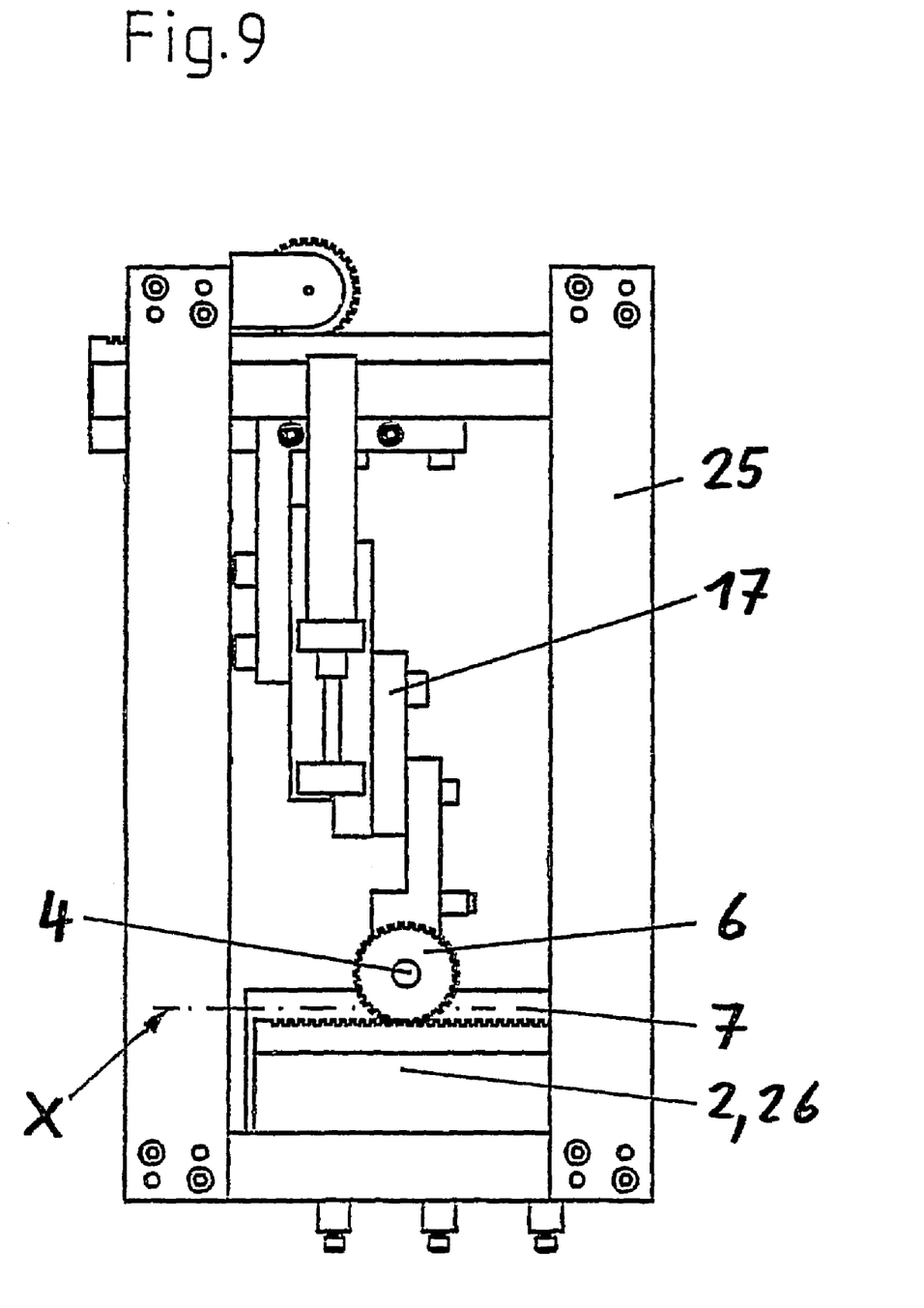
FIG. 9 shows a side view of the stimulating apparatus of FIG. 8.
Figure 10:
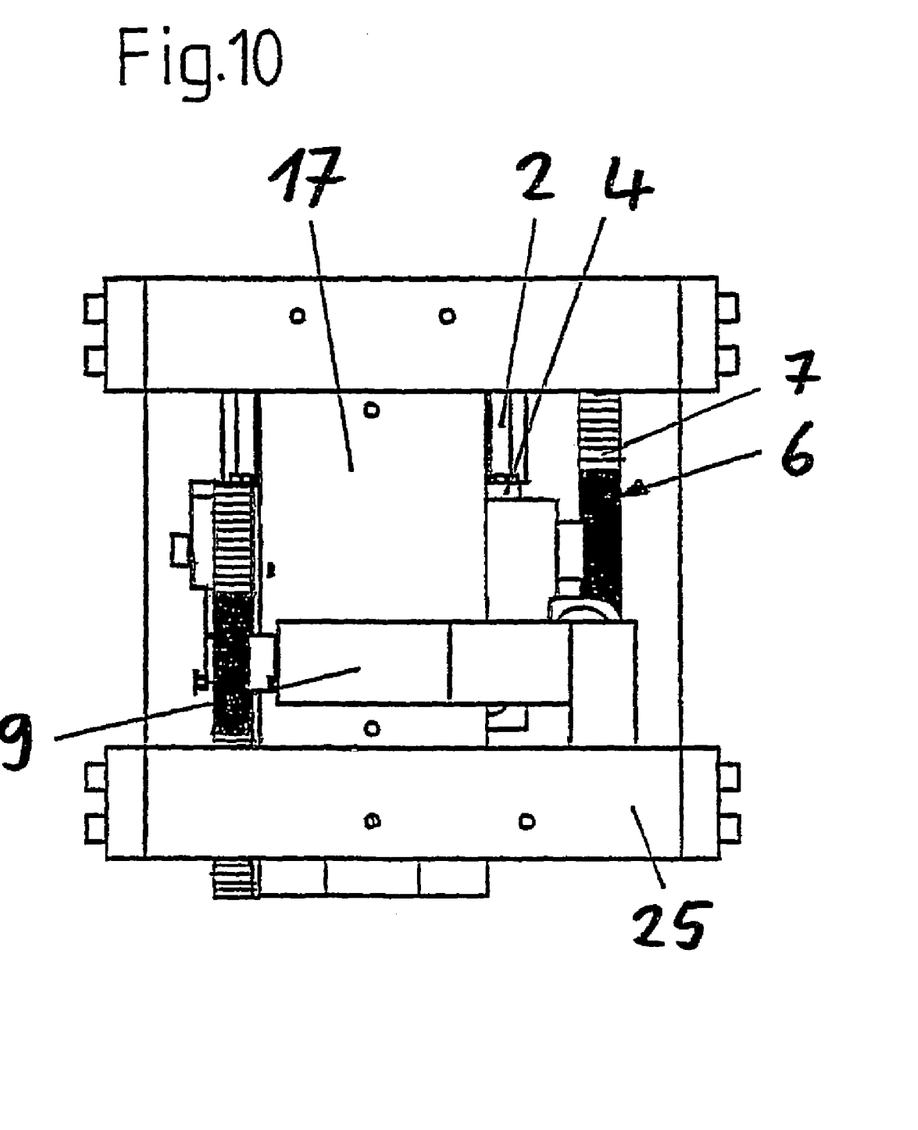
FIG. 10 shows a top view of the stimulating apparatus of FIG. 8.

The FIGS. 8 to 10 show different views of a first embodiment of a stimulating apparatus operating according to the schematics of FIG. 5. The apparatus comprises a sturdy framework 25 housing a tissue carrier 2, a roller 4 and a moveable support structure 17 for supporting the roller 4 and effecting a guided movement of it relative to the tissue carrier 2. The tissue carrier 2 is disposed within a nutrient solution basin 26 and has arranged at its topside, as shown in FIG. 5, a silicone slap 15 providing a planar receiving surface 11 with several recesses 12 for mounting several tissue patches 1 in such a manner that they present first surfaces 3 in a common horizontal plane X. The roller 4 has arranged at its periphery several second surfaces 5, which are separated by several flattenings 13. In order to facilitate the operating mode described in the discussing of FIG. 5, a geared servo motor 9 drives a gear wheel 18 which engages with the teeth of a gear rod 19 mounted on the support structure 17, thereby horizontally displacing the support structure 17 back and forth. The roller 4, which is rotatably supported in the support structure 17, has arranged at one end a gear wheel 6 having a effective pitch circle diameter that is bigger than the diameter of the roller 4 defined by its second surfaces 5. This gear wheel 6 engages the teeth of a gear rod 7 that is fixedly mounted to the framework 25, thereby causing the roller 4 to rotate clockwise and counter-clockwise while horizontally travelling forth and back. To adjust the compressive force imposed by the second surfaces 5 of the roller 4 on the receiving surface 11 and on the first surfaces 3 of the tissue patches 1, the support structure includes a vertical guide with a manually adjustable micrometer screw 20 for adjusting the vertical position of the roller 4.

Figure 11:
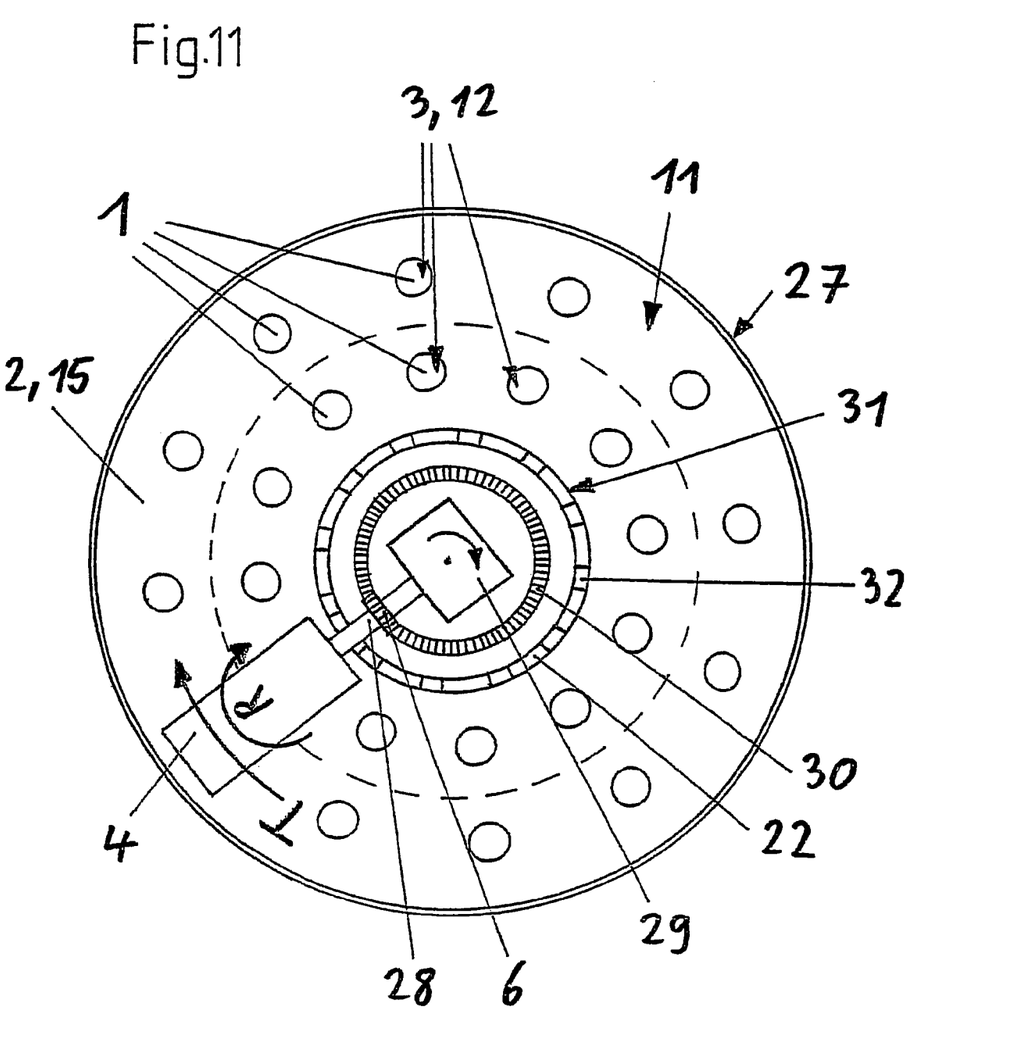
FIG. 11 shows a top view of a second embodiment of a stimulating apparatus according to the invention.

FIG. 11 shows a top view of a second embodiment of a tissue stimulating apparatus according to the invention. The tissue carrier 2 of this embodiment comprises an annulus shaped nutrient basin 27 and a flat silicon slab 15, which provides within said basin 27 an annulus shaped receiving surface 11 extending in a horizontal plane. The receiving surface 11 provides a plurality of cavities 12 arranged on two different diameters around the center defined by the receiving surface 11, in which tissue patches 1 are mounted in such a manner that they present first surfaces 3 to be stimulated in the horizontal plane of the receiving surface 11. The apparatus furthermore comprises a cylindrical roller 4 fixedly mounted to a roller shaft 28. The roller shaft 28 extends to the center defined by the receiving surface 11 where it is rotatably mounted to a driving end 29 of a drive shaft which rotates in said center perpendicular to the receiving surface 11 and the first surfaces 3. The drive shaft also presses the roller 4 with a specific compressive force towards the receiving surface 11 and the first surfaces 3. On the roller shaft 28 there is arranged, placed between the roller 4 and the driving end 29 of the drive shaft, a gear wheel 6 which engages the teeth of a gear rim 30 centered around the center of the receiving surface 11 and being non-rotatable with respect to the receiving surface 11 and the basin 27. Due to the rotation of the driving shaft, the roller 4 performs a horizontal travel motion T around the center of the receiving surface 11 and parallel to the plane defined by the first surfaces 3 of the tissue patches 1 and at the same time is rotated around its axis by the gear wheel 6. In the shown example, the diameter of the gear wheel 6 and the diameter of the roller 4 are dimensioned in such a fashion that at a medium diameter (indicated by a dotted line) around the center of the receiving surface 11, which is located between the two diameters on which the tissue patches 1 are arranged, the roller 4 performs a free rolling motion on the receiving surface 11 while at the diameters on which the tissue patches are arranged, its circumferential speed is lower or higher, respectively, than its speed of horizontal travel. By this, not only compressive and squeezing forces are imposed on the first surfaces 3 of the tissue patches 1 and on the receiving surface 11 but also shear forces. To frequently release these shear forces in order to relax a deformation of the silicone slab 15, the inner wall 31 of the basin 27 at its top side is embodied as a cam pathway 22 having arranged, in areas which are passed by the roller shaft 28 when the roller 4 is located between adjacent tissue patches 1, tappets 32 which lift the roller shaft 28 and with it the roller 4, the driving end 29 of the drive shaft and the gear rim 30, thereby temporarily spacing apart the roller 4 from the receiving surface 11 and releasing the shear forces. Embodying the tissue carrier 2 in this fashion leads to the advantage that the cam pathway 22 always corresponds to the tissue patch distribution pattern of the tissue carrier and that the use of tissue carriers with different tissue patch distribution patterns does not require a modification of the stimulation tools. Another advantage of this apparatus is, that the movement of all moving components is a continuous movement which does not require complicated and expensive, guiding means and controls and that a number of such apparatuses can be arranged in a space saving manner one upon the other using the same drive. By changing the direction of rotation of the drive shaft, opposing shear forces can be imposed. It is obvious for someone skilled in the art that the roller 4 might also be embodied as a conical roller and that all other principles discussed earlier, like e.g., flattenings arranged at the periphery of the roller or frictional wheels instead of gear wheels, can also be applied to an apparatus of this design.

Figure 12:
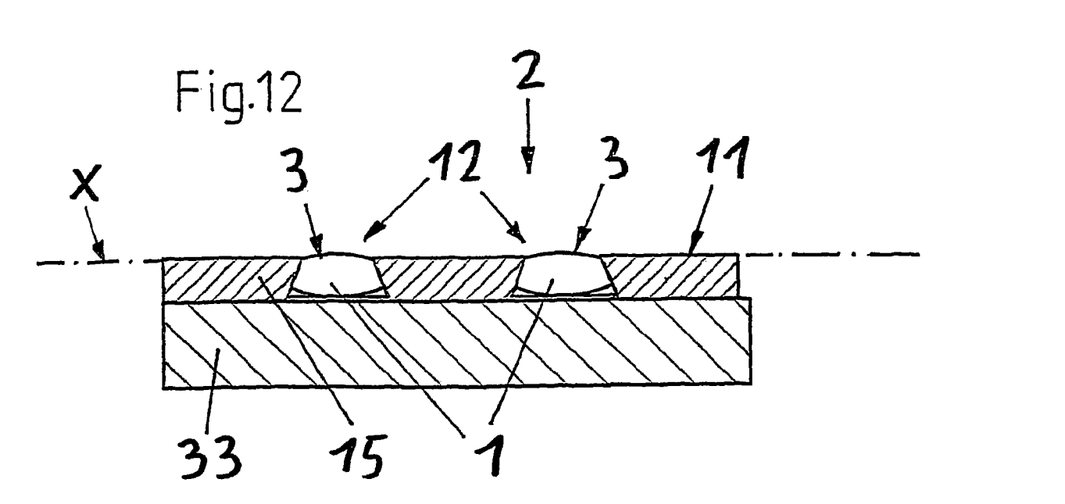
FIG. 12 shows a sectional view of a first tissue carrier according to the invention.
Figure 13:
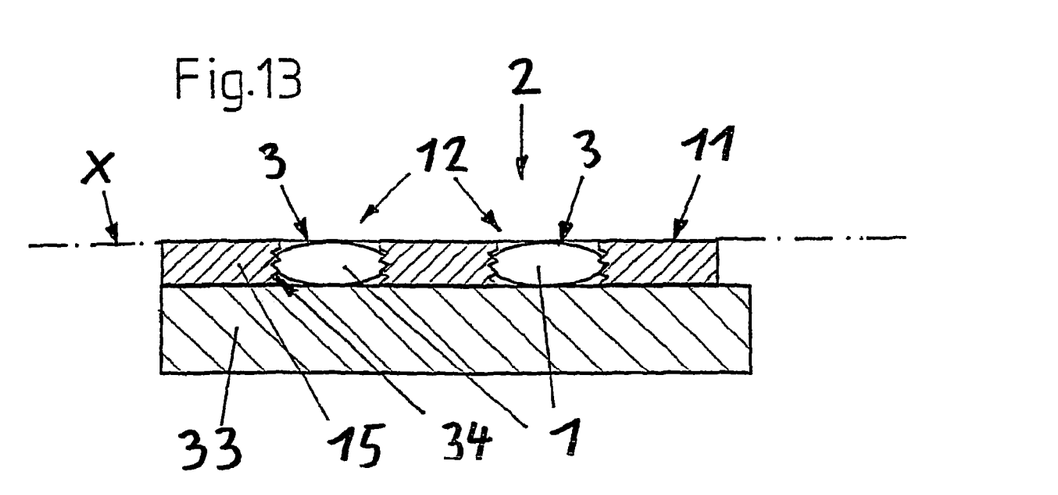
FIG. 13 shows a sectional view of a second tissue carrier according to the invention.
Figure 14:
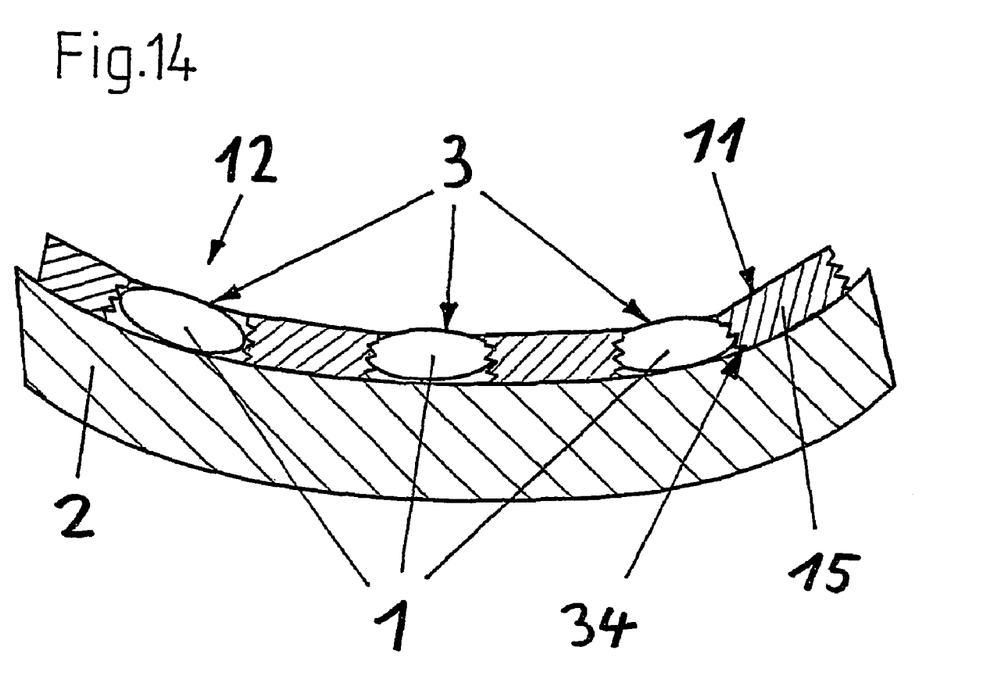
FIG. 14 shows a sectional view of a third tissue carrier according to the invention.

FIGS. 12 to 14 show different embodiments of tissue carriers 2 according to the invention. All of the shown tissue carriers 2 are formed by a support element 33, like e.g., a panel 33, and a slab 15 of elastic or visco-elastic material, like e.g. rubber, silicone, polyurethane or latex. The slab 15 forms a receiving surface 11 having several cavities 12 for receiving and mounting therein tissue patches 1 to be mechanically stimulated by imposing selected forces on first surfaces 3 presented by the tissue patches 1. The support element 33 supports the slab 15. It is, however, also possible to reinforce the slab 15 in such a manner, e.g. by forming it around a structure of metal wire or sheet metal, that it can be used without any support element 33.

In the embodiment shown in FIG. 12, the slab 15 and the cavities 12 in it have been formed by casting silicone into a mould. The cavities 12 have a conical shape and widen in direction from the receiving surface 11 to the bottom of the cavity 12, thereby permitting a retaining of the tissue patches 1 in the cavities by positive locking. The bottoms of the cavities 12 are arranged within the slab 15.

FIG. 13 shows an embodiment having as well a slab 15 made by casting. However, in this case, the cavities 12 penetrate through the slap 15 in a direction perpendicular to the receiving surface 11, so that their bottoms are formed by the panel 33. The walls of the cavities 12 have, in this embodiment, circumferential grooves 34 which as well allow a retaining of tissue patches 1 within the cavities 12 by positive locking.

The tissue carrier 2 shown in FIG. 14 employs the same principle as the one shown in FIG. 13, however, it is arched instead of being planar. It is also possible to embody such a tissue carrier as a tissue carrier drum, having arranged at its inside surface several cavities for receiving and mounting tissue patches 1.

While there are shown and described presently preferred embodiments of the invention, it is to be distinctly understood that the invention is not limited thereto but may be otherwise variously embodied and practiced within the scope of the following claims.

What is claimed:

1. A method for mechanical stimulation of tissue (1) in vitro, comprising the steps:
   providing one or several tissue patches (1) retained in a tissue carrier (2), thereby presenting one or several first surfaces (3) of said tissue patches (1);
   providing a roller type stimulating means (4) having arranged at its periphery one or several second surfaces (5); and
   effecting a relative movement between said roller type stimulation means (4) and said tissue carrier (2) for imposing specific forces on said first surfaces (3) through said second surfaces (5), thereby mechanically stimulating said tissue patches (1),
   wherein said first surfaces (3) are arranged in a common plane (X) and said relative movement includes a relative movement (T) parallel to said plane (X).

2. The method of claim 1, wherein said relative movement includes a rotation (R) of said roller type stimulation means (4) around its axis.

3. The method of claim 2, wherein said roller type stimulating means (4) is rotated at such rotational speeds that the circumferential speed at its second surfaces (5) at least temporarily differs from said speed of relative movement (T) parallel to said plane (X), thereby generating shear forces between said first (3) and second (5) surfaces.

4. The method of one of the claim 2, wherein the rotation (R) of said roller type stimulating means is mechanically coupled to said relative movement (T) parallel to said plane (X).

5. The method of claim 2, wherein said rotation (R) of said roller type stimulation means (4) is effected by drive means (8) which are separate from a drive (9) for the relative movement (T) parallel to said plane (X), in particular by an electric motor with speed and/or torque control.

6. The method of claim 2, wherein said rotation (R) of said roller type stimulating means (4) is effected by rolling said second surfaces (5) in frictional contact over said first surfaces (3) and/or over further surfaces (11) during said relative movement (T) parallel to said plane (X).

7. The method of claim 6, wherein shear forces are generated between said first surfaces (3) and second surfaces (5) by applying a specific brake force opposing said rotation (R) of said roller type stimulating means (4).

8. The method of claim 1, wherein a tissue carrier (2) is used which is formed by an elastic or visco-elastic material and has a receiving surface (11) having one or several recesses (12) for retaining patches of tissue (1) therein.

9. The method of claim 8, wherein said tissue patches (1) are retained within said recesses (12) in such a manner that said first surfaces (3) and said receiving surface (11) are commonly arranged within said plane (X).

10. The method of claim 3, wherein during relative movement (T) parallel to said plane (X), said shear forces are temporarily released to relax a deformation of said elastic or visco elastic material of said tissue carrier (2) caused by said shear forces.

11. The method of claim 10, wherein said release of shear forces is accomplished by temporarily spacing apart said roller type stimulating means (4) from said first (3) and/or receiving (11) surfaces.

12. The method of claim 10, wherein said release of shear forces is accomplished by temporarily releasing a rotational driving force or brake force applied to said roller type stimulating means (4).

13. The method of one of the preceding claims, wherein between said first surfaces (3) and said second surfaces (5), a deformable diaphragm (14) is arranged for forming an aseptic barrier between said first surfaces (3) and said second surfaces (5).

14. The method of one of the preceding claims, wherein tissue patches (1) are used which have been produced in vitro.

15. The method of one of the preceding claims, wherein patches of a cartilage or cartilage derived tissue (1) are used.

16. The method of one of the preceding claims, wherein the tissue patches (1) used are part of tissue/bone composites.

17. The method of one of the preceding claims, wherein at least said parallel relative movement (T) and the rotation (R) of said roller type stimulating means (4) are individually controlled, in particular by computerized control means, to achieve a specific stimulation cycle.

18. The method of claim 17 wherein the forces generated between said second surfaces (5) and said first surfaces (3) and/or said receiving surface (11) are measured and adjusted to predetermined values by controlling said movement (T) and/or said rotation (R).

* * * * *